(12) United States Patent
Jeon et al.

(10) Patent No.: US 9,024,000 B2
(45) Date of Patent: May 5, 2015

(54) METHOD TO IMPROVE THE SORBENT EFFICIENCY OF PROTEIN A CHROMATOGRAPHY USING SWITCHING COLUMN WITH CONTINUOUS FEEDING

(75) Inventors: Su Hi Jeon, Incheon (KR); Jin-Il Kim, Incheon (KR)

(73) Assignee: Celltrion, Inc., Incheon (KR)

( * ) Notice: Subject to any disclaimer, the term of this patent is extended or adjusted under 35 U.S.C. 154(b) by 297 days.

(21) Appl. No.: 13/643,146

(22) PCT Filed: Apr. 26, 2011

(86) PCT No.: PCT/KR2011/003015
§ 371 (c)(1),
(2), (4) Date: Oct. 24, 2012

(87) PCT Pub. No.: WO2011/136533
PCT Pub. Date: Nov. 3, 2011

(65) Prior Publication Data
US 2013/0046080 A1    Feb. 21, 2013

(30) Foreign Application Priority Data

Apr. 27, 2010   (KR) .................. 10-2010-0038745

(51) Int. Cl.
| | | |
|---|---|---|
| A23J 1/00 | (2006.01) |
| C07K 1/00 | (2006.01) |
| C07K 14/00 | (2006.01) |
| C07K 16/00 | (2006.01) |
| C07K 17/00 | (2006.01) |
| C07K 1/16 | (2006.01) |

(52) U.S. Cl.
CPC .. *C07K 1/16* (2013.01); *C07K 16/00* (2013.01)

(58) Field of Classification Search
None
See application file for complete search history.

(56) References Cited

U.S. PATENT DOCUMENTS

2004/0241878 A1   12/2004   Thommes

FOREIGN PATENT DOCUMENTS

| KR | 10-2006-0081422 A | 7/2006 |
| KR | 10-2007-0001969 A | 1/2007 |
| WO | 95-22389 A1 | 8/1995 |
| WO | 2008-153472 A1 | 12/2008 |

OTHER PUBLICATIONS

Millipore, "Affinity Chromatography Media" pp. 1-24, 2004.*

* cited by examiner

*Primary Examiner* — Daniel E Kolker
*Assistant Examiner* — James Rogers
(74) *Attorney, Agent, or Firm* — Lexyoume IP Meister, PLLC

(57) ABSTRACT

The present invention relates to a method to improve the sorbent efficiency of protein A chromatography using switching column with continuous feeding. In the chromatography method of the present invention, the increased usage efficiency of the absorbent (resin), the decreased processing time, the decreased operation cycle of column compared to that of single batch-type column, and the reduced amount of used resin are achieved and thus, the target protein can be purified at a high efficiency and a low cost.

8 Claims, 12 Drawing Sheets

Typical manufacturing process for mAb

US 9,024,000 B2

METHOD TO IMPROVE THE SORBENT EFFICIENCY OF PROTEIN A CHROMATOGRAPHY USING SWITCHING COLUMN WITH CONTINUOUS FEEDING

TECHNICAL FIELD

The present invention relates to a method to improve the sorbent efficiency of protein A chromatography using switching column with continuous feeding.

BACKGROUND ART

Recently, the market for a therapeutic monoclonal antibody has been grown very fast, and the productivity has increased sharply. Particularly, the development in cell line engineering technology and cell culturing technology increases the titer of culture solution to 10 g/L at a commercial scale.

In general, the chromatographic method used most-frequently for purifying the monoclonal antibody (mAb) in a biopharmaceutical field, includes the three steps of: 1) a protein A chromatography capturing selectively the mAb in the cell culture solution, 2) a cation exchange resin chromatography performed as a second step; and 3) an anion exchange resin chromatography as a final purification step (FIG. 1).

The protein A chromatography achieves a yield of 90% or higher and a purity of 99% or higher at a reference with Size Exclusion Chromatography (SEC) at only one purification time, because it has a very strong affinity to the mAb in the cell culture solution. Thus, the method is the most powerful tool for purifying the mAb using the chromatography.

The bottle neck step in the production of therapeutic mAb using the cell culture with a high titer lies in the purification step, more specifically protein A chromatography which has the following disadvantages due to the traditional batch-type operation:

1) The commercially-available protein A resin is very expensive and has very shorter life cycle than the other resin due to the use of protein as a ligand. When it operates in a batch-type, the packed resin is only used as about 30 to 50% due to the limited kinetics of the protein. The method requires about two or three times of column volume as that operated in equilibrium state;

2) Only one column is used in a batch-type and the steps of equilibrium, sample injection, washing, elution, regeneration and sterilization are carried out sequentially. The batch-type method requires relatively longer processing time and thus shows very low batch processing speed (FIGS. 2); and 3) The washing and elution steps need considerably large volume of buffer solution in the batch-type chromatography, but the buffer solution is made of water for injection, thereby causing an economical burden.

To solve the disadvantages of the batch-type chromatography and the problems caused by the high titer in the cell culture, there are recently various attempts to study the application of the Simulated Moving Bed (SMB) chromatography to the production of the therapeutic antibody.

SMB chromatography has been used largely for the petrochemical and the mineral field. Compared with the batch-type chromatography, SMB chromatography has various advantages such as a small volume of consumed buffer solution, a high productivity and a high concentration of the final product, and recently, has been actively studied for applying to the separation of biomaterials.

To apply SMB chromatography to the purification of bioengineering products, especially a protein, there are some problems to be previously settled as follows:

1) The loss of product is inevitable at an initial starting operation and final closing process of SMB chromatography. When it is applied for the production of product in a short campaign, the product loss is relatively higher than the batch-type chromatography;

2) It is difficult to define the batch which is very important for the production of biopharmaceuticals. In particular, the division of batch is basically difficult in the purification method which maintains the efficiency by continuously operating the cell culture according to the process principle;

3) It is not suitable for the process to produce various products for a short campaign. Generally, SMB chromatography uses at least four columns, and the patent owned by Biogen Idec uses at most twenty columns. There are some works for product change over in order to prevent the cross-contamination of the products in the transition step that the operation for the next product campaign cannot start, after the operation of previous product campaign terminates. The works include the change of all used parts made from rubber and plastic, and the preparation of the homogeneously packed column by changing the resin. Because SMB chromatography apparatus is very complex and employs many columns, a long time and a large labor are required for the transition step.

4) The mobile phase of SMB chromatography employs many columns, pumps and valves, which are controlled by the complex control system. It is difficult to stably maintain the operation parameters due to the troubles with the pumps or valves.

U.S. Pat. No. 7,220,356 and Comparison of protein A affinity sorbent II Mass Transfer properties, Alios Jungbauer et al, Journal of chromatography A, 1093(2005) pp.98-110 are provided as the references.

CONTENTS OF THE INVENTION

Problems to be Solved

An object of the present invention is to provide a method with increasing the usage efficiency of the absorbent, compared to the conventional batch-type chromatography.

Technical Means

According to an embodiment of the present invention, there is a method of performing a chromatography for obtaining a target protein, using the chromatography apparatus having the number of column (n) including an initial column and a final column (n>1, n is an integer), in which an injection step of loading a sample, a collection step including washing and elution, and a regeneration step are carried out and the sample flows from a front column to a next column and from the final column to the initial column; and comprising the steps of:

1) loading the sample on the initial column as a front column;

2) loading the sample passing the front column, on a first next column after the front column;

3) before washing the front column, stopping the loading the sample to the first next column from the front column and directly loading the sample on the first next column;

4) loading the sample passing the first next column, on a second next column after the first next column; and 5) before washing the first next column, stopping the loading the sample to the second next column from the first next column, and directly loading the sample on the second next column; and steps 1) to 5) are carried out repetitively from the initial column to the final column and from the final column to the initial column, and the washing, elution and regeneration are performed in each column, with stopping the loading on the next column following each column.

EFFECT OF THE INVENTION

In the chromatography method of the present invention, the increased usage efficiency of the absorbent (resin), the decreased processing time, the decreased operation cycle of column compared to that of single batch-type column, and the reduced amount of used resin are achieved and thus, the target protein can be purified at a high efficiency and a low cost.

BEST MODE FOR CARRYING OUT THE INVENTION

The present invention will be described in more detail.

The present inventors invented a chromatography apparatus including a plural of columns (for examples, two or three columns) to resolve the problems of a single column batch-type chromatography, and compared the purification results obtained by performing a single column batch-type chromatography with 2 column or 3 column chromatography.

As a result, in the 2 column chromatography apparatus, the processing time per a batch for the bioreactor titer of 1.0 g/L to 10.0 g/L, was an equal to or shorter than the control system of single column batch-type chromatography. The number of operation cycle was decreased by 30 to 50% due to the achievement of maximum usage efficiency of resin (absorbent).

In the 3 column chromatography apparatus, the processing time per a batch for the bioreactor titer of 3.0 g/L to 10.0 g/L was an equal to or shorter than the control system, and the number of operation cycle was decreased by 30 to 50% due to the achievement of maximum usage efficiency of resin (absorbent).

The present inventors found that the chromatography apparatus and method of the present invention was an alternative system to satisfy the need for purifying the cell culture solution with high titer at a high efficiency and a high processing volume, and completed the present invention.

The chromatography apparatus of the present invention is described below in more detail.

Figure 8:
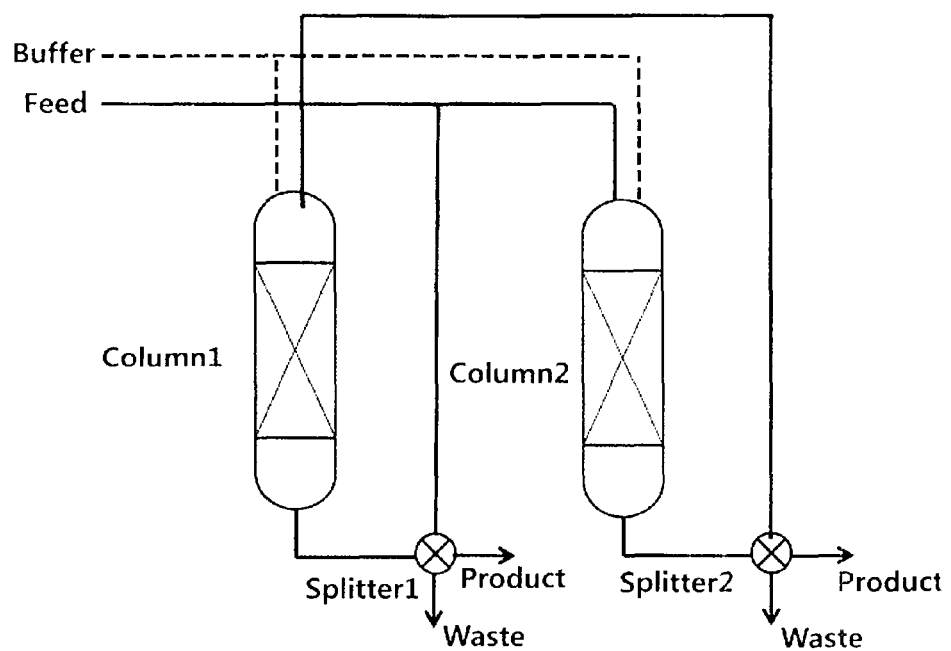
FIG. 8 is a schematic view of 2 column chromatography apparatus.
Figure 9:
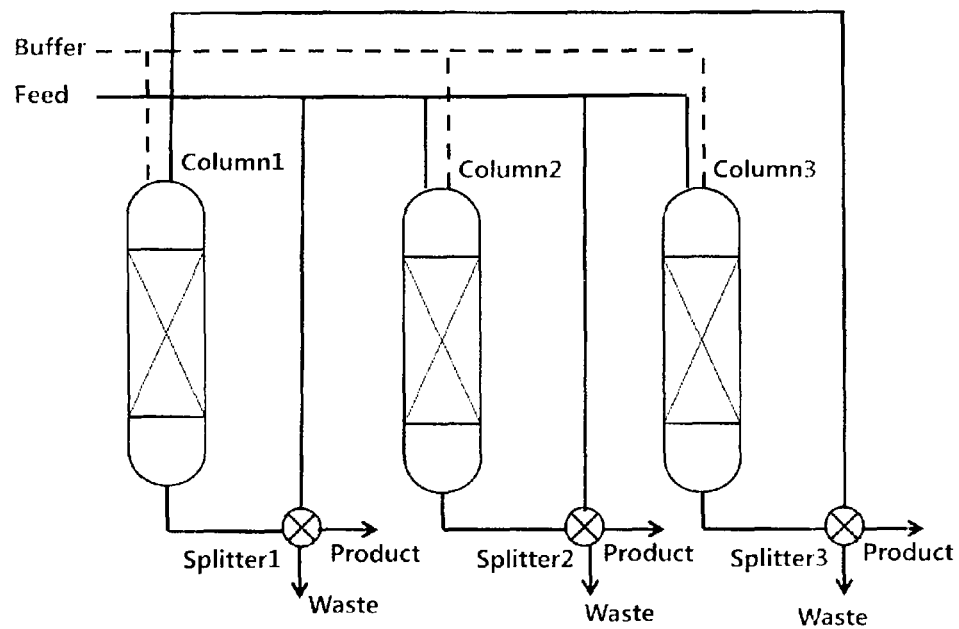
FIG. 9 is a schematic view of 3 column chromatography apparatus.
Figure 10:
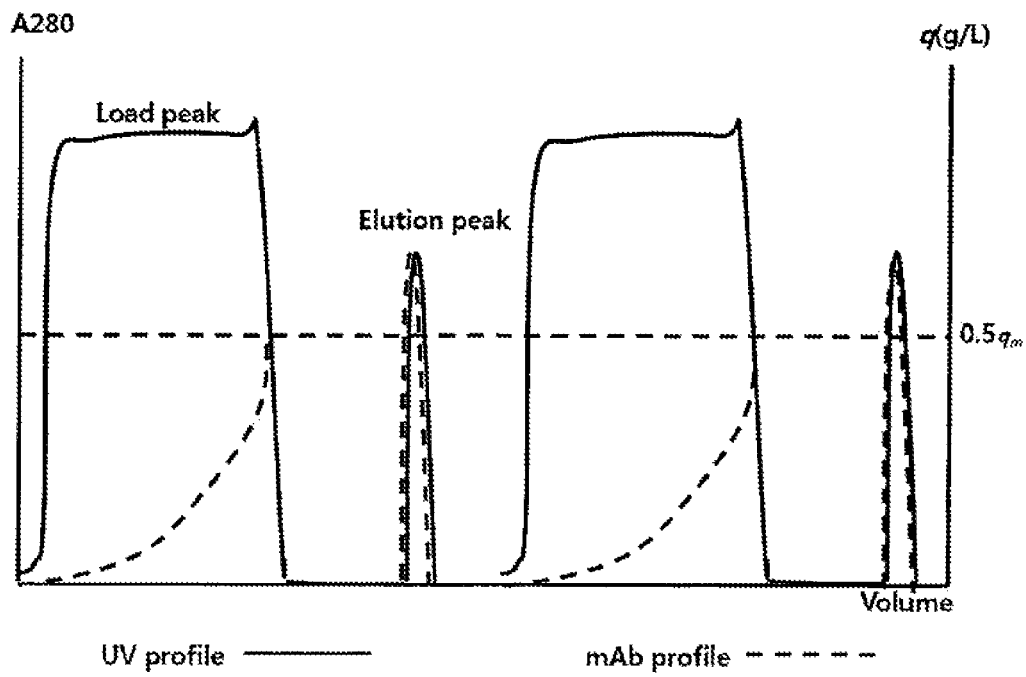
FIG. 10 is a graph of single column batch-type chromatography.
Figure 11:
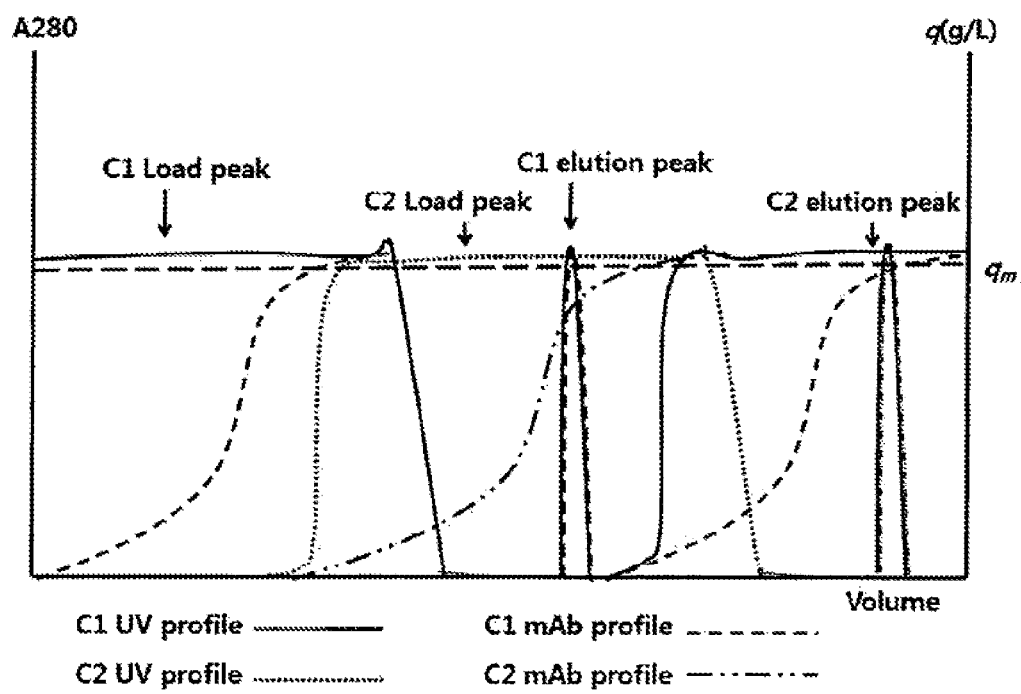
FIG. 11 is a graph of 2 column chromatography apparatus.
Figure 12:
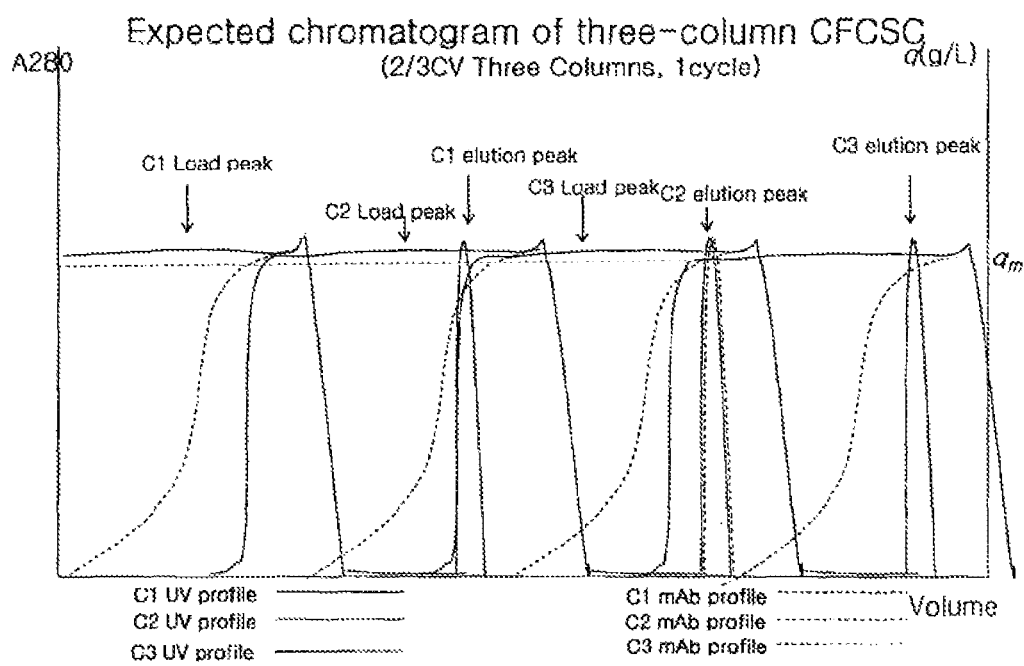
FIG. 12 is a graph of 3 column chromatography apparatus.

In each column of the chromatography apparatus, there are two independent inlets. One inlet is used for only injection of cell culture solution, and the other inlet is used for injecting various buffer solutions used in Protein A batch (FIGS. 8 and 9).

The cell culture solution is injected continuously and the injected buffer solutions are sequentially changed in each step in a batch.

The columns are connected serially and the distributor divides the liquid flow from the column into an inlet of waste water treatment, a tank for a product collection, or an inlet of another column.

The 2 column chromatography apparatus of the present invention can be operated as follow.

Figure 1:
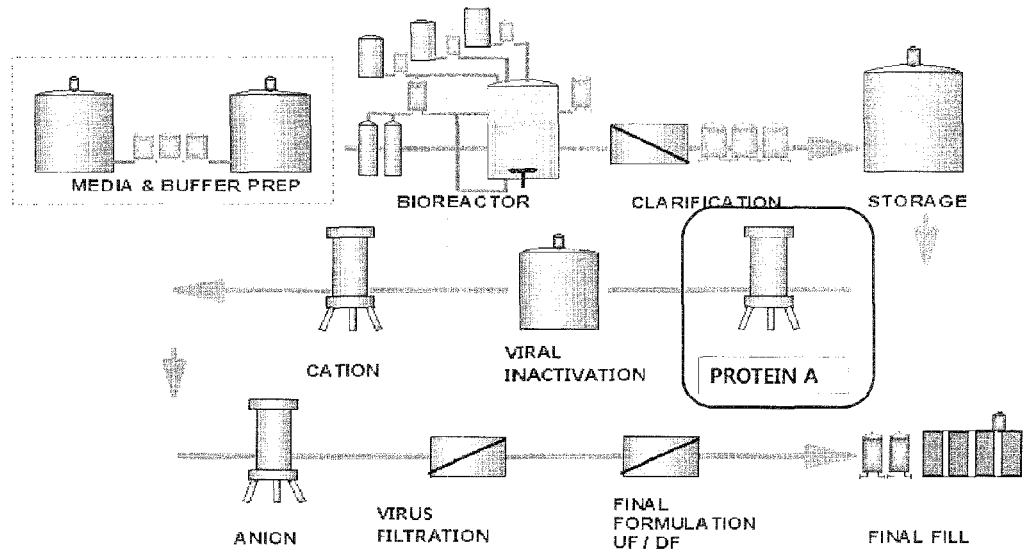
FIG. 1 shows a process for producing a therapeutic monoclonal antibody.
Figure 2:
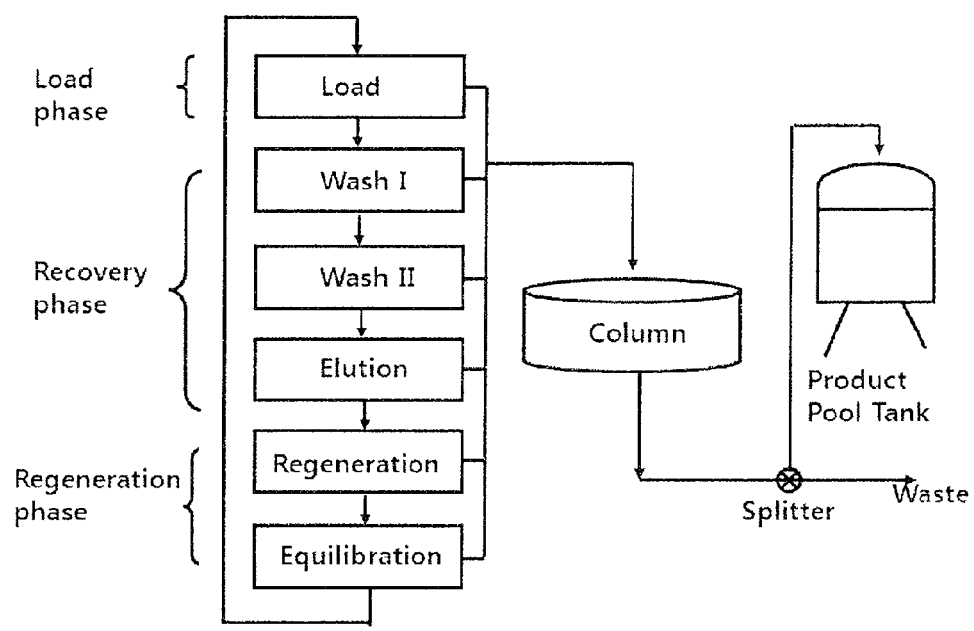
FIG. 2 is a schematic diagram of protein A batch-type chromatography.
Figure 3:
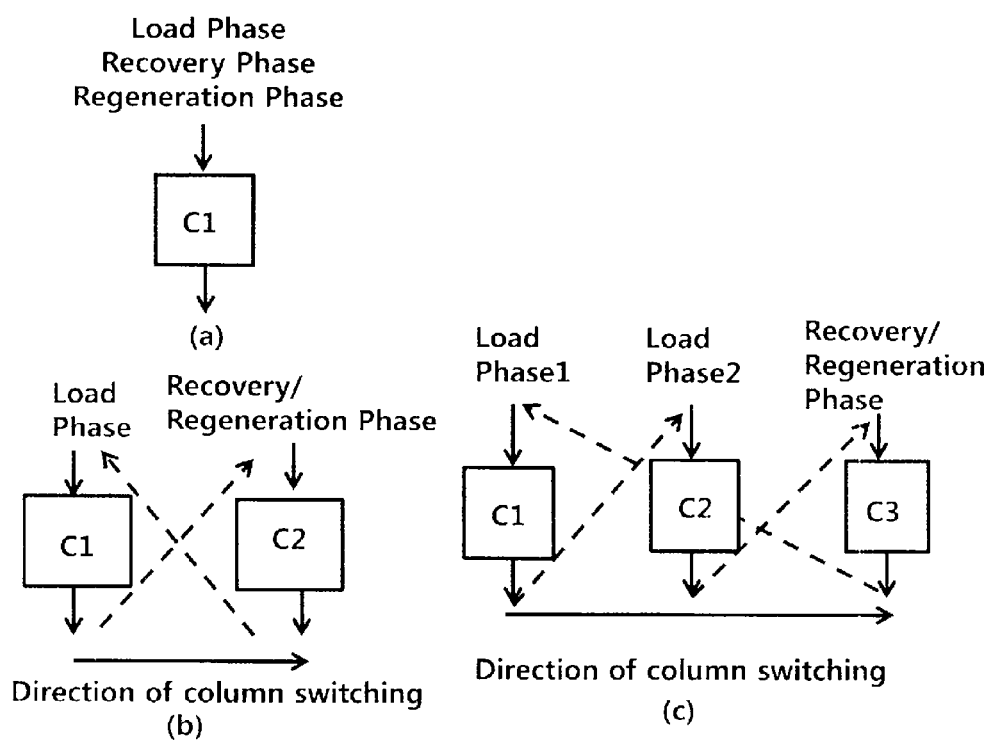
FIG. 3 is a schematic diagram of single column batch-type chromatography, and a schematic diagram of two column chromatography apparatus and three column chromatography apparatus:(a) conventional single column batch-type chromatography apparatus; (b) two column chromatography apparatus; and (c) three column chromatography apparatus.
Figure 4:
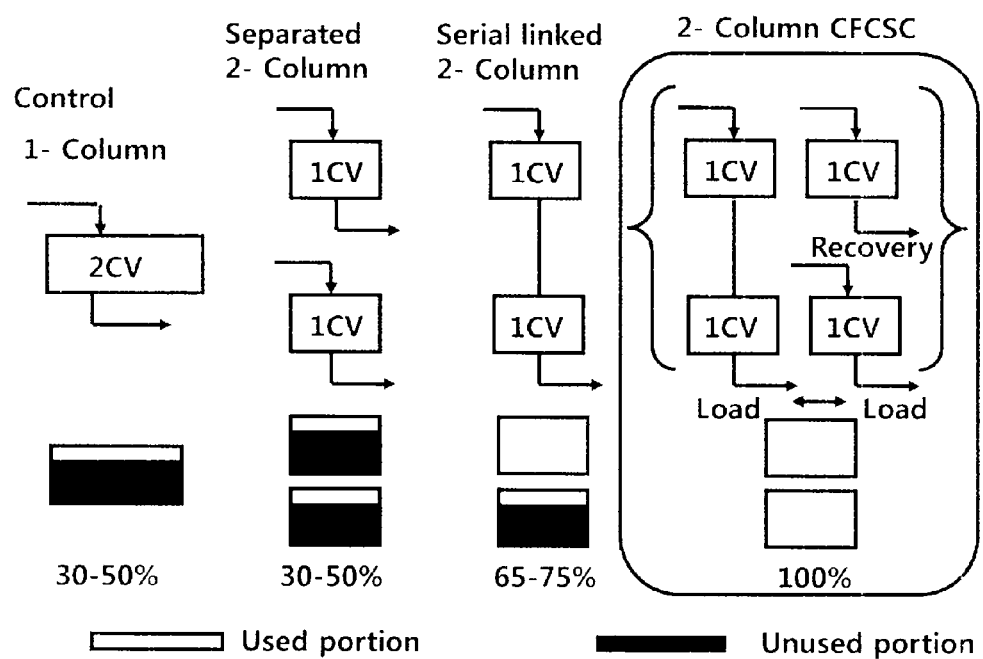
FIG. 4 shows the comparison result of the usage efficiency of resin in each apparatus.
Figure 5:
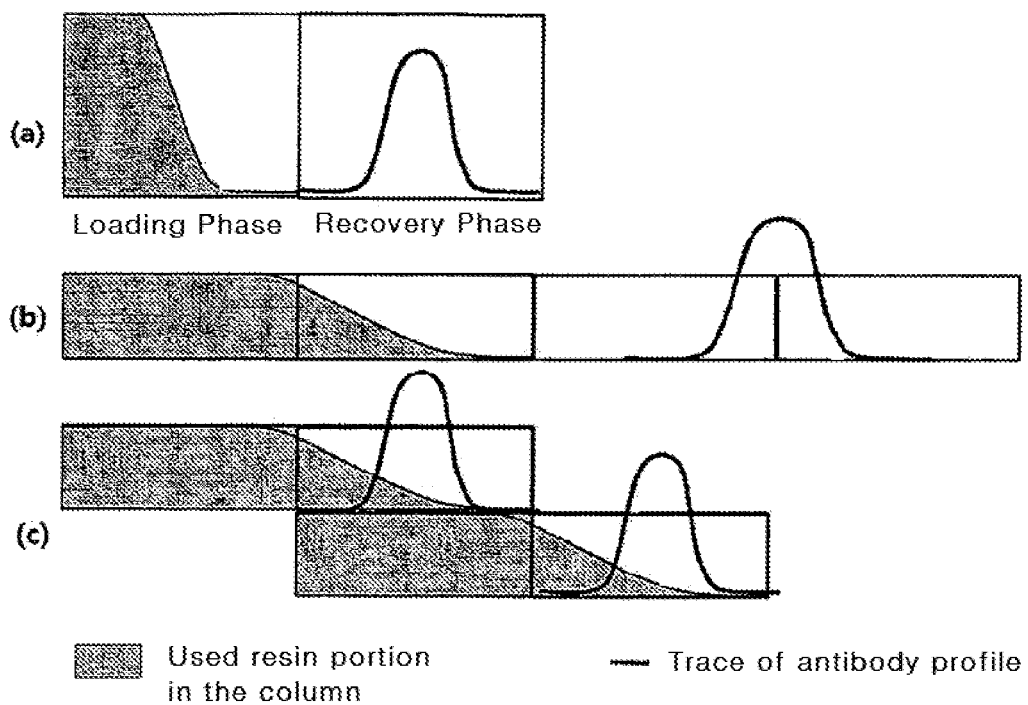
FIG. 5 shows the comparison result of the usage efficiency of resin and the productivity in each apparatus.
Figure 6:
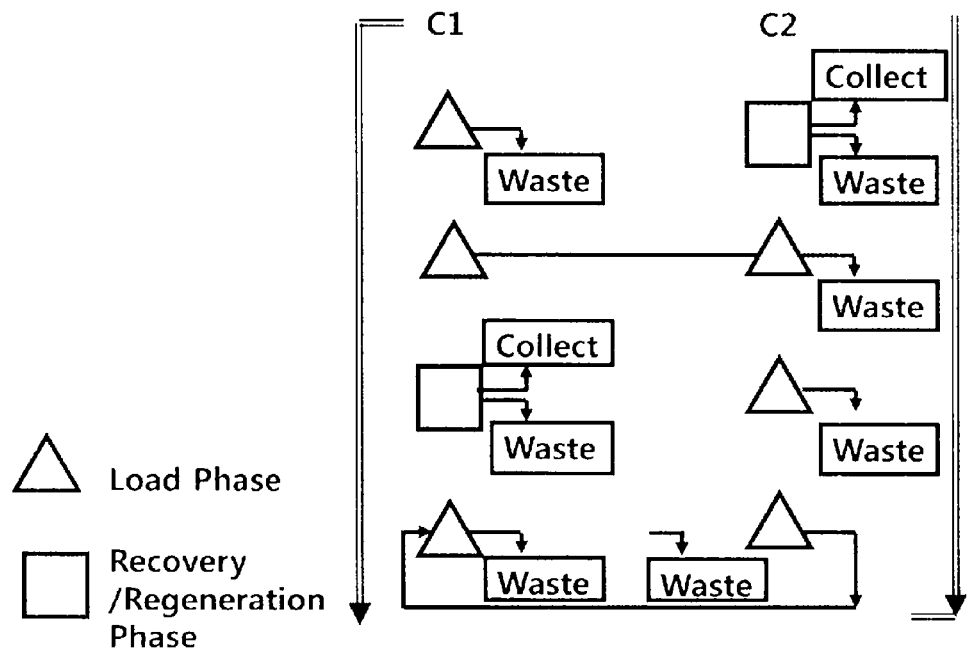
FIG. 6 is a schematic diagram of the operation of 2 column chromatography apparatus.

2 column chromatography apparatus (FIG. 6) is designed firstly for the cell culture solution with lower than 3.0 g/L cell of titer, but can be used for the higher titer.

As the injection step, the filtered cell culture is injected at a maximum biding capacity of the equilibrium state, and the product discharged from the first column is continuously injected to the second column.

After the first column absorbs the product at a maximum level, it is separated from the second column, and enters the collection step.

At that moment, the cell culture solution is injected into the second column at a maximum binding capacity, and the turnover of column is operated repetitively until the complete consumption of cell culture solution.

In the collection step, the product is collected and the column is regenerated for the next cycle.

In the preferred embodiment of the present invention, the method of purifying a target protein using the chromatography apparatus including two columns, includes the steps of:

1) loading a sample on the first column;

2) loading an unabsorbed fluid from the first column, on the second column which is connected to the first column in series;

3) after injecting the sample on the first column to the maximum static binding capacity (qm) of the first column, while the target protein is collected from the first column and the first column is regenerated in a state of being disconnected from the second column, loading the sample on the second column;

4) after the regeneration of the first column in step 3) is completed, loading an unabsorbed fluid from the second column on the first column by connecting the second column to the first column in series;

5) after injecting the sample on the second column to the maximum static binding capacity (qm) of the second column, while the target protein is collected from the second column and the second column is regenerated in a state of being disconnected from the first column, loading the sample on the first column; and 6) operating the steps 1) to 5) repetitively until the complete consumption of the sample.

Figure 7:
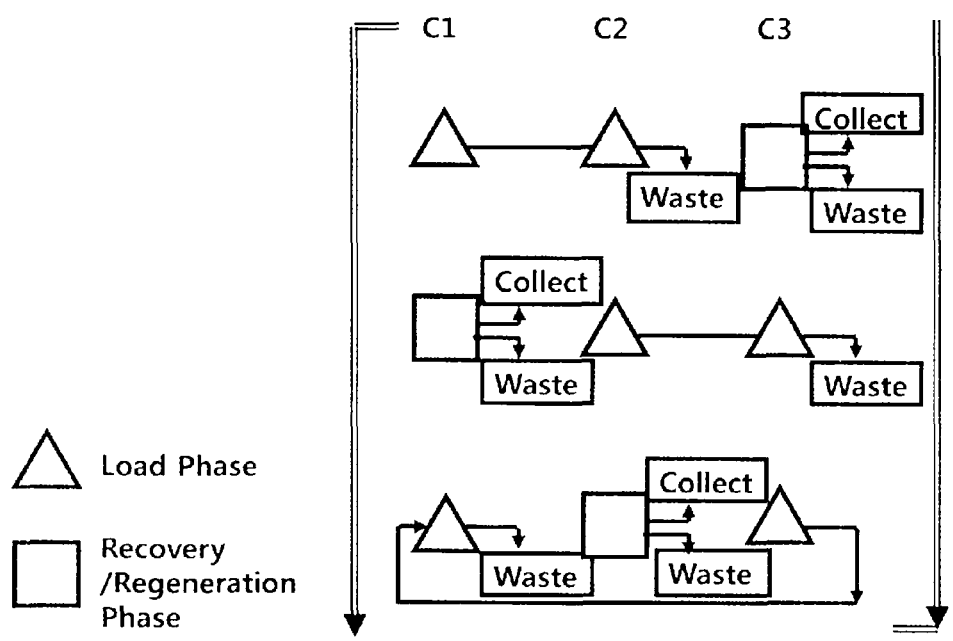
FIG. 7 is a schematic diagram of the operation of 3 column chromatography apparatus.

3 column chromatography apparatus (FIG. 7) is designed for the cell culture solution with 3.0 g/L cell titer or higher, and has a shorter injection time of cell culture than the cell culture solution with lower cell titer, in case that the same volume of bioreactor is used.

At the sample injection step, the filtered cell culture is injected at a maximum biding capacity of the equilibrium state, and the unabsorbed sample discharged from the first column is continuously injected to the second column.

After the first column absorbs the product at a maximum level, it is separated from the second column, and enters the collection step. At that moment, the cell culture solution is injected into the second column at a maximum binding capacity, and the unabsorbed fluid discharged from the second column is continuously injected to the third column pretreated with the equilibrium state.

The next turn-over of column starts, when the injection of the sample completes to the second column. At that time, the first column enters the regeneration step for the next cycle. The turn-over cycle is operated repetitively until the complete consumption of cell culture solution.

In the preferred embodiment of the present invention, the method of purifying a target protein using the chromatography apparatus including two columns includes the steps of:

1) loading a sample on the first column;
2) loading an unabsorbed fluid from the first column, on the second column which is connected to the first column in series;
3) after injecting the sample on the first column to the maximum static binding capacity (qm) of the first column, while the target protein is collected from the first column and the first column is regenerated in a state of being disconnected from the second column, loading the sample on the second column and an unabsorbed fluid from the second column on the third column which is connected to the first column via the second column;
4) after the regeneration of the first column in step 3) is completed, loading an unabsorbed fluid from the third column on the first column by connecting the third column to the first column in series;
5) after injecting the sample on the second column to the maximum static binding capacity (qm) of the second column, while the target protein is collected from the second column and the second column is regenerated in a state of being disconnected from the third column, loading the sample on the third column;
6) after the regeneration of the second column in step 5) is completed, connecting the first column to the second column in series;
7) after injecting the sample on the third column to the maximum static binding capacity (qm) of the third column in step 6), while the target protein is collected from the third column and the third column is regenerated in a state of being disconnected from the first column, loading the sample on the first column;
8) after the regeneration of the third column in step 7) is completed, connecting the second column to the third column in series; and 9) operating the steps 1) to 8) repetitively until the complete consumption of the sample.

Various examples of the present invention will be described.

The chromatography of the present invention can further include a middle column of chromatography used in obtaining a target protein in which the injection step of loading a sample, the collection step including washing and elution and the regeneration step are carried out in the column, the sample is loaded on the middle column from the distributor of the initial column; an inlet of the middle column for loading a sample; and a distributor of the middle column for distributing the sample which is loaded through the inlet of the middle column and pass through the middle column.

In the chromatography apparatus of the present invention, the distributor of initial column can load the sample passing the initial column on the final column.

In addition, in the chromatography apparatus of the present invention, the distributor of middle column can load the sample passing the middle column on final column.

At the loading step of sample, preferably, the examples of target proteins include a monoclonal antibody, an immunoglobulin and a recombinant protein, but not limited thereto.

In an embodiment, the column includes a solid phase to be loaded with sample where the solid phase is made of protein A or protein G.

The washing solution is preferably a buffer solution with a low concentration of salt, or a buffer solution with a high concentration of salt. More preferably, the solution with the low concentration of salt is 10 mM to 50 mM buffer added with 0.001 mM to 100 mM of NaCl, and the solution with high concentration of salt is 50 mM to 100 mM buffer added with 0.001 mM to 1 M of NaCl.

The elution solution is preferably an acidic elution solution.

A Clean in place (CIP) solution is used as a regeneration solution, and the CIP solution contains a phosphoric acid or a citric acid.

Hereinafter, the actions and effects of the present invention will be illustrated in more detail by means of the following examples. However, these examples are provided only to assist the understanding of the present invention and it is not intended for the scope of the present invention to be limited in any manner by them.

EXAMPLE 1

In order to prove the effectiveness of the present invention, as shown in Table 1, the standard of commercially-used column and resin were determined, and adsorption isotherm parameter determining the resin binding capacity were calculated according to the disclosure of R. Halm et al., J. Chromatogr, A 1093(2005), pp. 98-100).

The titers of the cell culture solution in bioreactor were applied with 0.3 g/L, 1.0 g/L, 3.0 g/L and 10.0 g/L by reflecting the information of Matt Crougham Keck Graduate Institute which was cited by Genentech in IBC 2008, and the usage volume of bioreactor 12,500 L which has been used generally in the industrial field. The diameter of column was determined by the numerical value of the representative column used in the industrial field, and the bed height of column was 22.2 cm used in the industrial field. The flow rate of the buffer solution was 300 cm/hr of linear speed which was the maximum flow rate of MabSelect Xtra® resin. The injection capacity per cycle of chromatography was 35 g/L, which was 90% of maximum dynamic binding capacity of MabSelect Xtra® resin for the single batch-type column used as a control system, and was 80% of maximum static binding capacity (qm) for 2 column chromatography apparatus and 3 column chromatography apparatus.

TABLE 1

Model process parameters

| Category | Step parameters |
|---|---|
| Cell culture fluid volume | 12,000 L |
| Antibody titer | 0.3, 1.0, 3.0, 10.0 g/L |
| protein A resin | Mabselect Xtra(r) |
| Column bed height | 22.2 cm |
| Linear flow rate | 300 cm/hr |
| Control Column ID | 45, 60, 100, 140, 200 cm |
| maximum dynamic binding capacity (DBCm) | 40 (mg/mL) |
| adsorption isotherm | Langmuir($q = qmd(c + Kd)$) |
| maximum static binding capacity (qm) | 68.3 (mg/mL) |
| Equilibrium Dissociation constant: Kd | 0.088 (mg/mL) |
| The injection capacity for Control single column | 90% DBCm |
| The injection capacity for 2 column or 3 column CFCSC | 80% qm |
| Diameter of resin particle(dp) | 75 μm |
| Total porosity (εb) | 0.92 |
| Internal porosity of resin particle(εα) | 0.87 |

The diameter of column and number of column were shown in table 2 for the titer of each bioreactor.

TABLE 2

| Injection titer (g/L) | 1 column batch-type column ID(cm) | 1 column batch-type column volume (L) | 2 column column ID(cm) | 2 column column volume (L) | 3 column column ID(cm) | 3 column column volume (L) |
|---|---|---|---|---|---|---|
| 0.3 | 45 | 34.7 | 31.6 | 17.4 × 2 | 25.8 | 11.6 × 3 |
| 1.0 | 60 | 62.8 | 42.4 | 31.4 × 2 | 34.6 | 20.9 × 3 |
| 3.0 | 100 | 174.4 | 70.7 | 87.2 × 2 | 57.7 | 58.1 × 3 |
| 10.0 | 140 | 341.7 | 99.0 | 170.9 × 2 | 80.8 | 113.9 × 3 |
| — | 200 | 697 | 141.4 | 38.7 × 2 | 115.4 | 232.3 × 3 |

The optimum cycle number of chromatography depending on the operation conditions, and the amount of used resin, the volume of used buffer solution, and the operation time were calculated and the general operating order and the kinds of buffer solutions were summarized in Table 3.

TABLE 3

Unit step of chromatography and volume of buffer solution

| Unit step | Volume of buffer solution (column volume) | Flow rate (cm/hr) |
|---|---|---|
| Pre Sanitization | 4.01 CV | 300 |
| Pre Regeneration | 4.01 CV | 300 |
| Equilbration | 5.01 CV | 300 |
| Loading | 1,2500/Cycle no.[1] (L) | 300 |
| Re-Equilibration | 4.01 CV | 300 |
| Wash | 6.01 CV | 300 |
| Elution | 3 CV | 200 |
| Regeneration | 4.01 CV | 300 |
| Sanitization | 4.01 CV | 300 |
| Neutralization | 3.01 CV | 300 |
| Storage | 4.01 CV | 300 |

[1] Single column batch-type chromatography, Cycle no = RoundUp(Titer(g/L)/0.9 DBCm/column vol.(L))
2-column or 3-column chromatography apparatus Cycle no = RoundUp(Titer(g/L)/0.8 qm/column vol.(L)).

As a result of calculating the cycle number according to the formulae, the optimum cycle number of chromatography for the control system and the experimental systems were obtained and shown in Table 4. In the experimental systems, the cycle number of the operation was decreased by 33% to 50%, compared to those of control system under all conditions.

TABLE 4

The calculated cycle number of chromatography operation for each group

| Simulation condition | bioreactor titer(g/L) | column internal diameter (mm) | column volume (L) | Cycle/Batch 1 column | Cycle/Batch 2 column | Cycle/Batch 3 column |
|---|---|---|---|---|---|---|
| 1 | 0.3 | 450 | 35 | 4 | 2 | 2 |
| 2 | 1.0 | 600 | 63 | 6 | 4 | 4 |
| 3 | 1.0 | 1000 | 174 | 3 | 2 | 2 |
| 4 | 3.0 | 1400 | 342 | 4 | 2 | 2 |
| 5 | 10.0 | 2000 | 697 | 6 | 4 | 4 |

The calculated amount of consumed resin was summarized in Table 5. In the experimental systems, the amount of the operations was decreased by 33% to 50% compared to those of control system.

The simulation was based on the assumption that the resin packed at a time could be used to at least 200 cycles, and the annual productivity could be 60 batches,

TABLE 5

The calculated annual amount of consumed resin

| Simulation condition | bioreactor titer(g/L) | column internal diameter (mm) | column volume (L) | Annual amount of used resin(L/year) 1 column | 2 column | 3 column |
|---|---|---|---|---|---|---|
| 1 | 0.3 | 450 | 35 | 42 | 21 | 21 |
| 2 | 1.0 | 600 | 63 | 113 | 75 | 75 |
| 3 | 1.0 | 1000 | 174 | 157 | 105 | 105 |
| 4 | 3.0 | 1400 | 342 | 410 | 205 | 205 |
| 5 | 10.0 | 2000 | 697 | 1255 | 836 | 836 |

The calculated amount of used buffer solution per a batch was summarized in Table 6. In the 2-column chromatography apparatus, the amount was decreased by 22% to 42% of that of control system, and the amount in 3-column chromatography apparatus was decreased by 29% to 40% of the control system in the ranges of 3.0 g/L to 10.0 g/L of bioreactor titer.

TABLE 6

| Simulation condition | bioreactor titer(g/L) | column internal diameter (mm) | column volume (L) | Annual amount of used resin (L/year) 1 column | 2 column | 3 column |
|---|---|---|---|---|---|---|
| 1 | 0.3 | 450 | 35 | 4995 | 3452 | 4066 |
| 2 | 1.0 | 600 | 63 | 11773 | 9235 | 10233 |
| 3 | 1.0 | 1000 | 174 | 16524 | 12557 | 13150 |
| 4 | 3.0 | 1400 | 342 | 40364 | 23458 | 24052 |
| 5 | 10.0 | 2000 | 697 | 116666 | 82340 | 83352 |

The calculated operation time under each condition was shown in Table 7, and the operation time for 2-column chromatography apparatus was equal to that of control system at 1.0 g/L bioreactor titer, and was decreased by maximum 48% at 3.0 g/L. In case of 3-column chromatography apparatus, the calculated operation time increased by 123% of that of control system at 1.0 g/L or less, but was decreased by 18% at 3.0 g/L and 63% at 10.0 g/L.

TABLE 7

The calculated operation time for each
batch in the experimental systems

| Simulation condition | bioreactor titer(g/L) | column internal diameter (mm) | column volume (L) | Operation time for each batch(hr/batch) | | |
|---|---|---|---|---|---|---|
| | | | | 1 column | 2 column | 3 column |
| 1 | 0.3 | 450 | 35 | 38 | 55 | 84 |
| 2 | 1.0 | 600 | 63 | 30 | 31 | 48 |
| 3 | 1.0 | 1000 | 174 | 14 | 12 | 20 |
| 4 | 3.0 | 1400 | 342 | 14 | 7 | 12 |
| 5 | 10.0 | 2000 | 697 | 17 | 11 | 6 |

The invention claimed is:

1. A method of purifying a target protein using a chromatography apparatus consisting of two columns including a first column and a second column, the method comprising:
   1) loading a sample on the first column;
   2) loading an unabsorbed fluid from the first column, on the second column which is connected to the first column in series;
   3) after injecting the sample on the first column to the maximum static binding capacity (qm) of the first column, loading the sample on the second column while the target protein is collected from the fist column and the first column is regenerated in a state of being disconnected from the second column;
   4) after the regeneration of the first column in step 3) is completed, loading an unabsorbed fluid from the second column on the first column by connecting the second column to the first column in series;
   5) after injecting the sample on the second column to the maximum static binding capacity (qm) of the second column, loading the sample on the first column while the target protein is collected from the second column and the second column is regenerated in a state of being disconnected from the first column; and
   6) performing the steps 1) to 5) repetitively until the complete consumption of the sample.

2. The method of claim 1, wherein the target protein is a monoclonal antibody, and immunoglobulin, or a recombinant protein.

3. The method of claim 1, wherein the columns include a solid phase to be loaded with sample where the solid phase is made of protein A or protein G.

4. The method of claim 1, further comprising washing at least the first column or second column with a 10 mM to 50 mM washing buffer solution comprising 0.001 mM to 100 mM NaCl.

5. The method of claim 1, further comprising washing at least the first column or second column with a 50 mM to 100 mM washing buffer solution comprising 0.001 mM to 1 mM NaCl.

6. The method of claim 1, further comprising eluting the target protein with an elution solution which includes an acidic buffer solution.

7. The method of claim 1. wherein the the first column and the second column are generated with a regeneration solution which is a Clean in place (CIP) solution.

8. The method of claim 7, wherein the CIP solution contains a phosphoric acid or a citric acid.

* * * * *